United States Patent [19]

Lafon

[11] 4,146,647
[45] Mar. 27, 1979

[54] SUBSTITUTED PHENYL-AMIDINES

[75] Inventor: Louis Lafon, Paris, France

[73] Assignee: Laboratoire L. Lafon, Maisons Alfort, France

[21] Appl. No.: 762,774

[22] Filed: Jan. 25, 1977

[30] Foreign Application Priority Data

Jan. 26, 1976 [GB] United Kingdom ............... 2895/76

[51] Int. Cl.² .................... A61K 31/16; C07C 123/00
[52] U.S. Cl. .................................... 424/326; 544/242;
544/315; 544/318; 544/330; 544/332; 544/335;
260/308 D; 260/562 N; 260/564 G; 548/347;
548/351; 548/352; 548/353
[58] Field of Search ...................... 260/564 G, 562 N;
424/326

[56] References Cited

U.S. PATENT DOCUMENTS

| 3,115,525 | 12/1963 | D'Alo | 260/256.4 G |
| 3,234,255 | 2/1966 | Hackmann et al. | 260/256.4 G |
| 3,394,181 | 7/1968 | Bell | 260/256.4 G |
| 3,855,249 | 12/1974 | Lafon | 260/256.4 G |

Primary Examiner—Donald G. Daus
Assistant Examiner—James H. Turnipseed

[57] ABSTRACT

The present invention provides compounds of the formula:

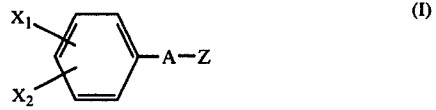

in which A is $CH_2$, CHOH, $CH_2O$, $CH_2S$, $CH_2NH$, $OCH_2$, $SCH_2$, NH, $NHCH_2$, $NHCOCH_2$ or $CH_2NHCH_2$, $X_1$ is H, halogen, $C_1$-$C_4$-alkyl or $C_1$-$C_4$-alkoxy, $X_2$ is halogen, $C_1$-$C_4$-alkyl or $C_1$-$C_4$-alkoxy, Z is 2-pyrimidinyl or $C(=NR_1)NHR_2$ (where $R_1$ is H and $R_2$ is H, OH or $CH_2CO_2Et$, or $R_1$ and $R_2$ together form $CH_2CH_2$, $CH_2CH_2CH_2$ or N=N), and their addition salts. The compounds of formula I and their salts are useful in therapy as hypotensive agents.

11 Claims, No Drawings

SUBSTITUTED PHENYL-AMIDINES

The present invention relates to substituted phenyl-amidines and their addition salts, to their production, and to their therapeutic use.

The new compounds of the invention are: the substituted phenyl-amidines of the general formula:

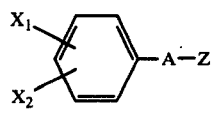   (I)

in which A represents the —CH₂—, —CHOH—, —CH₂O—, —CH₂S—, —CH₂NH—, —OCH₂—, —SCH₂—, —NH—NHCH₂, —NHCOCH₂— or —CH₂NHCH₂— group, X₁ represents a hydrogen atom, a halogen atom (preferably Cl or F), a C₁-C₄-alkyl group (preferably C₃), or a C₁-C₄-alkoxy group (preferably OCH₃ and OC₂H₅), X₂ represents a halogen atom (preferably Cl or F), a C₁-C₄-alkyl group (preferably CH₃), or a C₁-C₄-alkoxy group (preferably OCH₃ and OC₂H₅), and Z represents the 2-pyrimidinyl group or the group

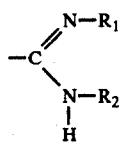

(where R₁ represents H, R₂ represents H, OH or CH₂CO₂C₂H₅, and R₁ and R₂ considered together can form a group chosen from amongst —CH₂CH₂—, —CH₂CH₂CH₂— and —N=N—), and their addition salts, including not only addition salts with acids but also quaternary ammonium salts, especially those obtained by reacting the free base with an alkyl halide such as CH₃I, C₂H₅I, CH₃Cl or CH₃Br.

The cyclic or non-cyclic functional amidino groups have been represented arbitrarily above, by the nitrogen-containing group (a) in order to facilitate comprehension of the text, though in general the said group (a) is in equilibrium with the group (b):

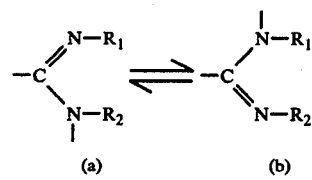

(a)    (b)

The preferred compounds according to the invention are those in which the group Z represents the following functional groups:

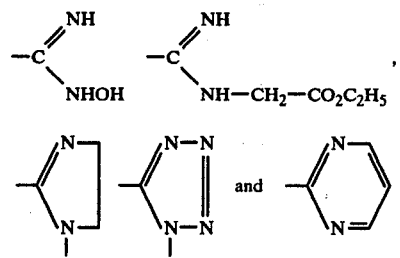

Some compounds of the formula I according to the invention are listed by way of illustration in Table I which follows:

TABLE I

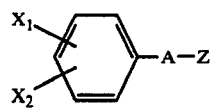

| Example | Code No. | X₁ | X₂ | A | Z | Addition salt | Melting point |
|---|---|---|---|---|---|---|---|
| 1 | CRL 1752 | 3-Cl | 4-Cl | CHOH | —C(=NH)NHCH₂CO₂C₂H₅ | hydrochloride | 203° C |
| 2 | CRL 40056 | 2-Cl | 6-Cl | CHOH | (tetrazole) | hydrochloride | 160–165° C |
| 3 | CRL 40089 | 3-Cl | 4-Cl | CH₂ | (imidazoline) | hydrochloride | 227–228° C |
| 4 | CRL 40102 | 3-Cl | 4-Cl | CH₂ | —C(=NH)NHOH | hydrochloride | 146° C |
| 5 | CRL 40236 | 2-Cl | 6-Cl | NHCOCH₂ | —C(=NH)NHOH | hydrochloride | 220° C |
| 6 | CRL 40243 | 2-Cl | 6-Cl | CH₂NH | (pyrimidinyl) | hydrochloride | 188° C |

TABLE I-continued

| Example | Code No. | $X_1$ | $X_2$ | A | Z | Addition salt | Melting point |
|---|---|---|---|---|---|---|---|
| 7 | CRl 40255 | 2-Cl | 6-Cl | $CH_2S$ | 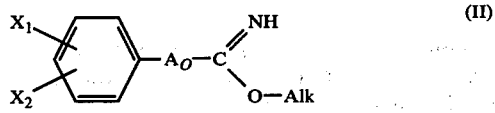 | hydrochloride | 260° C (a) |
| 8 | CRl 40256 | 2-$CH_3$ | 6-$CH_3$ | NH | —C(=NH)NHOH | hydrochloride | — |
| 9 | CRl 40264 | 3-$OCH_3$ | 5-$OCH_3$ | $OCH_2$ | 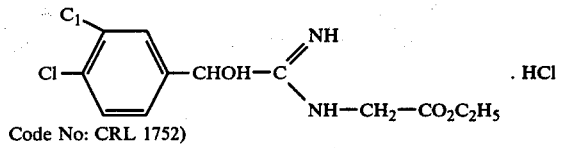 | hydrochloride | — |
| 10 | CRl 40306 | 2-Cl | 6-Cl | NH | —C(=NH)NHOH | hydrochloride | 200° C |
| 11 | CRl 40344 | 2-Cl | 6-Cl | $CH_2NHCH_2$ | —C(=NH)NHOH | dihydrochloride | 174° C |
| 12 | CRL 40315 | 3-$OC_2H_5$ | 5-$OC_2H_5$ | $OCH_2$ | —C(=NH)NHOH | hydrochloride | 174–176° C (a) |
| 13 | CRL 40375 | 3-Cl | 4-Cl | $NHCH_2$ | —C(=NH)NHOH | hydrochloride | 160–162° C |
| 14 | CRL 40424 | 4-Cl | H | $NHCH_2$ | —C(=NH)NHOH | dihydrochloride | 150° C |
| 15 | CRL 40469 | 3-F | H | $NHCH_2$ | —C(=NH)NHOH | dihydrochloride | 126–128° C |

Note (a): with decomposition

The compounds of the formula I can be prepared in accordance with a feature of the invention by methods A and B, shown below:

Method A comprises the reaction of an imino-alkyl-ether of the formula:

 (II)

(where $X_1$ and $X_2$ are defined as above, $A_O$ represents a —$CH_2$—, —CHOH—, —$CH_2NH$—, —$OCH_2$—, —$SCH_2$—, —NH—$NHCH_2$, $NHCOCH_2$— or —$CH_2NHCH_2$— group an Alk is a $C_1$–$C_4$ alkyl group), in the form of the hydrochloride, with an amine compound which is $H_2NR_2$, $H_2NCH_2CH_2NCH_2$, $H_2NCH_2CH_2CH_2NCH_2$ or

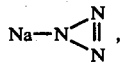

in a $C_1$–$C_4$ alkanol in the presence of HCl.

The Imino-alkyl-ether of the formula II can be prepared by reaction of the corresponding nitrile with an alkanol in the presence of HCl and be isolated before the reaction, or be prepared in situ without being isolated.

Method B consists of reacting a compound of the formula:

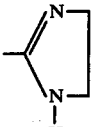 (III)

(where $X_1$ and $X_2$ are defined as above and $A_1$ preferably represents a —$CH_2$— group) with an amidino derivative of the formula:

H — X — $T_1$ (IV)

(where X is NH or S, and $T_1$ represents 2-pyrimidinyl, 2-$\Delta^2$-imidazolinyl or 2-(1,4,5,6-tetrahydropyrimidinyl).

The invention includes within its scope therapeutic compositions which contain at least one compound of the formula I, or one of its non-toxic addition salts, in association with a physiologically acceptable excipient. The compounds of the formula I are, as a group, hypotensive agents which are useful in the treatment of hypertension. Certain compounds — in particular the product of Example 3 (CRL 40089) — act on the central nervous system, especially as anti-depressants.

The following Examples illustrate the invention.

EXAMPLE 1

Ethyl (3,4-dichloromandelamidino)-acetate hydrochloride

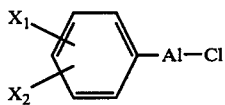

Code No: CRL 1752)

(a) 3,4-Dichloromandelimino-ethyl-ether.

100 g (0.59 mol) of 3,4-dichlorobenzaldehyde, 15 ml of sodium bisulphite in aqueous solution, traces of o-cresolsulphone-phthalein and 170 ml of demineralised water are introduced into a 1 liter three-neck flask equipped with a central mechanical stirrer, and on one side neck a two-branch adapter surmounted by a dropping funnel and a condenser provided with a calcium chloride guard tube, and on the other side neck another dropping funnel. At the same time, in order to maintain the colour of the reaction mixture within the colour-change range of the indicator (pH 7.4 to 8.8), 150 ml of a 4 N hydrochloric acid solution and 40 g of potassium cyanide dissolved in 150 ml of water are added.

When the addition is complete, stirring is continued for 1 hour at ordinary temperature (15°–25° C.) and the organic lower oil is extracted with 2 × 350 ml of ether. The organic phase is washed with water until the pH of the wash waters is neutral, and is then dried over sodium sulphate 60 ml of ethanol are added to the dry solution in ether, containing the 3,4-dichloro-mandelonitrile, and 30 g (0.85 mol) of dry hydrogen chloride gas are then absorbed in the organic solution by bubbling into the latter. After allowing the solution to stand over the weekend at ordinary temperature and then added 200 ml of ether, 105 g of 3,4-dichloromandelimin-oethyl-ether hydrochloride are obtained by filtration.

Melting point 150° C. (with decomposition).
Yield: 61.5%.

(b) CRL 1752.

A solution of sodium methylate prepared from 4.95 g of sodium (0.215 mol) is added dropwise, whilst maintaining the temperature of the reaction at about 4° C., to 30 g (0.215 mol) of ethyl aminoacetate hydrochloride dissolved in 100 ml of methanol. When the addition is complete, the alcoholic solution is filtered and then evaporated under a waterpump vacuum, without exceeding 30°-35° C. The residue is taken up in 100 ml of ether and the solution is again filtered and evaporated to dryness. 18 g of ethyl aminoacetate base (which is unstable and should be used during the following 12 hours) are thus obtained.

14.2 g (0.05 mol) of 3,4-dichloromandelimino-ethyl-ether hydrochloride and 100 ml of ethanol are introduced into a 250 ml flask equipped with a magnetic stirrer, the alcoholic solution is cooled to 5° C. on an ice bath and 6 g (0.058 mol) of ethyl aminoacetate (base) are then added all at once.

After leaving the reactants in contact for 5 hours whilst stirring at 5° C., and then overnight in a refrigerator, the solution is evaporated to dryness and the residue is taken up in 100 ml of 3 N hydrochloric acid and 100 ml of ethyl acetate. The insoluble matter is filtered off. 7.5 g of LL 1752 are thus obtained.

Melting point = 203° C. Yield = 44%. Nitrogen determination (Kjeldahl): N calculated = 8.2% N found = 7.9%.

Amine determination in acetic acid by means of perchloric acid: Amine equivalent calculated = 341.5. Amine equivalent found = 346.

EXAMPLE 2

2-(α-Hydroxy-2,6-dichlorobenzyl)-tetrazole hydrochloride

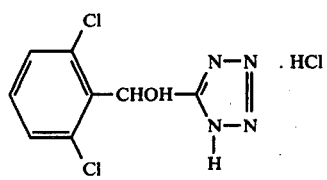

Code No: CRL 40056

A solution of 2.3 g (0.035 mol) of sodium azide and 9.5 g (0.35 mol) of 2,6-dichloromandelimino-methyl-ether in 100 ml of methanol is stirred for 2 hours at 20° C. The precipitated sodium chloride is filtered off and the filtrate is evaporated to dryness in vacuo. The residue is taken up in 50 ml of water and the product is filtered off, washed with water and recrystallised from ethanol. The base, dissolved in 50 ml of ethanol, is acidified with a solution of hydrogen chloride in ethanol and the product is filtered off and recrystallised from methanol.

CRL 40056 is obtained in the form of a white powder, in a yield of 80%.

Instantaneous melting point = 160°-165° C.

EXAMPLE 3

2-(3,4-Dichlorobenzyl)-Δ²-imidazoline hydrochloride

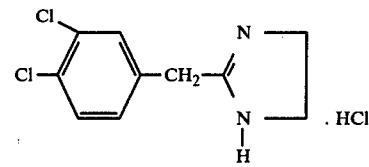

Code No: CRL 40089

(a) 3,4-Dichlorophenyl-acetonitrile 2 l of ethanol and 977.5 g (5 mols) of 3,4-dichlorobenzyl chloride are charged into a 10 l reactor. The mixture is heated until it starts to reflux and 6 mols of potassium cyanide dissolved in 750 cm³ of water are run in slowly over the course of 2 hours. The reflux is maintained for 1 hour. A further mol of cyanide is added over the course of 40 minutes and the mixture is heated under reflux for a further 30 minutes. It is then cooled and diluted with water. The nitrile which precipitates as an oil is decanted. The aqueous phase is washed with 2 l of diisopropyl ether and the organic solution is added to the oil. The solution of the nitrile in diisopropyl ether is washed with twice 1.5 l of water. This solution is collected over 125 g of anhydrous magnesium sulphate and 12.5 g of carbon black. The mixture is stirred, left to stand and filtered. The filter is washed with 3 l of diisopropyl ether, which are added to the solution of the nitrile.

(b) 2-(3,4-Dichlorophenyl-1-imino-1-methoxy-ethane hydrochloride

The solution of the preceding nitrile is charged into a 10 l reactor. 1 liter of diisopropyl ether is distilled and 176 g (5.5 mols) of anhydrous methanol are added. Hydrochloric acid gas is bubbled in, whilst keeping the temperature of the reaction mixture at between 20° and 30° C. After the imino-ether hydrochloric has precipitated, the passage of HCl gas is continued for 1 hour after which the mixture is cooled in ice so as to bring it down to about 5° C. It is filtered and the product is washed with twice 800 cm³ of diisopropyl ether, suction-drained and dried in a vacuum over at about 40° C.

Weight of imino-ether hydrochloride = 981 g (3.85 mols).

Yield relative to 3,4-dichlorobenzyl chloride = 77.1%.

Instantaneous melting point (Kofler) = 110°-115° C. with decomposition.

This product must be employed rapidly in the next stage.

(c) 2-(3,4-Dichlorobenzyl)-Δ²-imidazoline 5 l of isopropanol and the preceding imino-ether are charged into a 10 l reactor. 462 g (7.7 mols) of ethylenediamine are added and the mixture is heated under reflux for 3 hours. 5 l of isopropanol are then distilled and 6 l of an aqueous HCl solution are then run slowly onto the remaining suspension until a pH less than or equal to 1 is obtained. This solution is washed with three times 1 l of diisopropyl ether and is run slowly, with violent stirring, into 1.5 l of NaOH (d = 1.33) diluted with 5 l of water. The crystallisation is seeded by means of the free base of CRL 40089 prepared beforehand, and the mixture is allowed to crystallise. The crystals are filtered off and washed by twice working them into a paste with 4 l of water. They are then filtered off and washed with water until the wash waters are neutral. The base is dried in a vacuum oven at 40° C. A weight of "crude base" of 718 g is obtained.

(d) CRL 40089

The base is dissolved in 4.8 l of anhydrous ethanol in the presence of 14 g of carbon black and the mixture is left under reflux for 30 minutes. It is filtered hot and hydrogen chloride gas is bubbled in whilst hot, until the pH is less than or equal to 2. The mixture is allowed to crystallise and to cool to about 5°-8° C. The product is filtered off, suction-drained and washed with three times 500 cm³ of anhydrous ethanol. It is dried in a vacuum oven at 40° C.

The first crop gives a weight of 576 g of CRL 40089.

The filtrate is concentrated to about 2.5 l, boiled for 15 minutes with 2 g of carbon black, filtered hot and left to cool to about 8° C. It is then filtered again and the product is suction-drained, washed with three times 75 cm³ of anhydrous ethanol and dried in a vacuum oven at 40° C.

A second crop of 76 g of CRL 40089 is obtained.

Total weight of CRL 40089 = 652 g (2.46 mols)

Yield relative to the imino-ether = 63.9%.

Yield relative to 3,4-dichlorobenzyl chloride = 49.2%.

White flaky crystalline powder.

Instantaneous melting point (Kofler) = 227°-228° C.

% Cl⁻ = 13.38% (theory = 13.37%).

EXAMPLE 4

3,4-Dichlorophenyl-acetamidoxime hydrochloride

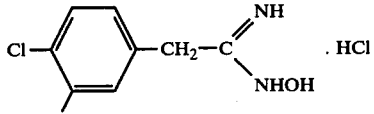

Code No: CRL 40102

200 ml of methanol and 75 ml of water are introduced into a 500 ml flat-bottomed flask, with magnetic stirring. The mixture is cooled to 10° C. and stirred slowly. A mixture of 100 g of potassium bicarbonate and 69.5 g (1 mol) of hydroxylamine hydrochloride is added in small amounts. Carbon dioxide is evolved and the temperature reaches −5° C. Stirring is maintained until the evolution of CO₂ has ended. The KCl, which is insoluble in this mixture, is filtered off and the precipitate is washed with twice 75 ml of methanol.

The solution of the hydroxylamine base is introduced into a 1 liter three-neck flask equipped with a mechanical stirrer, condenser and dropping funnel. The solution is cooled to 0° C. and stirred slowly. The whole of the nitrile, dissolved in methanol (0.424 mol), is added and the mixture is kept at 0° C. for 2 hours.

At the end of this time, a solution of hydroxylamine base is prepared from 100 ml of CH₃OH, 37.5 ml of water, 50 g of KHCO₃ and 35 g of hydroxylamine hydrochloride, the KCl is then filtered off and the precipitate is washed with twice 20 ml of CH₃OH. This solution is introduced into the reaction mixture and the whole is stirred at 0° C. for 14 hours and for the week-end at ambient temperature (15°-25° C.).

Thereafter, 400 ml of water and 200 ml of concentrated hydrochloric acid are added to the mixture, followed by changing the vessel and adding 750 ml of water. The mixture is stirred for 1 hour. A small amount of insoluble matter is filtered off and the methanol is driven off on a rotary evaporator. A small amount of insoluble matter is again filtered off. The aqueous solution is neutralised with 270 g of sodium hydroxide solution. An oily precipitate appears, which is extracted with three times 200 ml of ether. The ether is evaporated and the traces of NH₂OH are thoroughly driven off on a rotary evaporator. The residue is taken up in ether and the ether is dried over Na₂SO₄ overnight.

The hydrochloride of the product is precipitated by means of 100 ml of a 5 N solution of hydrogen chloride in ether. The precipitate is filtered off, washed with refluxing ethyl acetate and dried. 10.8 g of CRL 40102 are obtained.

Melting point = 146° C.

Yield = 10%.

EXAMPLE 5

2,6-Dichloroformanilido-acetamidoxime hydrochloride

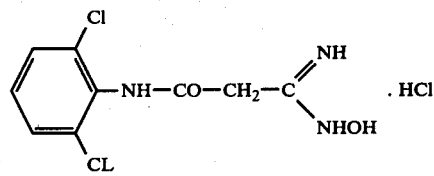

Code No: CRL 40236

(a) α-Chloro-2,6-dichloroacetanilide 0.3 mol (50 g) of 2,6-dichloro-aniline and 300 ml of pure acetone are introduced into a 1,000 ml three-neck flask. 0.45 mol (50.85 g) of chloroacetyl chloride are run in over the course of 17 minutes, whilst stirring. The mixture is heated under reflux for 15 minutes. After the end of the introduction of the acid chloride, the mixture is cooled. 210 ml of a solution of 100 g of K₂CO₃ and 310 ml of H₂O are run in. The solution obtained is poured into a 200 ml Erlenmeyer flask containing 300 ml of H₂O, and some ice. A precipitate forms. The product which has precipitated is filtered off and dried. 67.8 g of α-chloro-2,6-dichloro-acetanilide of the formula:

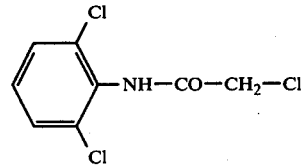

are obtained.

Yield = 94%

(b) α-Cyano-2,6-dichloroacetanilide 20.28 g (0.312 mol) of KCN are dissolved in 170 ml of distilled water in a 1,000 ml Erlenmeyer flask, whilst stirring magnetically and cooling. A solution of 67.8 g (0.284 mol) of the preceding halogen derivative in 500 ml of a 95:5 v/v C₂H₅OH—H₂O mixture is run in over the course of 1 hour. The mixture is heated for 4 hours under reflux and is cooled. The ethanol is driven off on a rotary evaporator. The residual aqueous phase is extracted with three times 100 ml of CHCl₃. A material which is insoluble both in water and chloroform is filtered off. It consists of virtually the whole of the expected nitrile. It is dried.

Weight = 17.4%.
Yield = 26%.

(c) CRL 40236

A solution of 17.06 g (0.316 mol) of NaOCH₃ in methanol and a solution of 22 g (0.316 mol) of hydroxylamine hydrochloride in methanol are mixed whilst being cooled by means of an ice bath. The mixture is stirred for 10 minutes and the NaCl is filtered off. The filtrate is introduced into a 1,000 ml Erlenmeyer flask, with magnetic stirring and cooling by means of an ice bath. Into this solution is run a solution of 17.4 g (0.076 mol) of the nitrile obtained under (b), in methanol. The mixture is left stirring overnight.

Thin layer chromatography, using the following:
Eluant [C₆H₆:CH₃COCH₃ (50:50) v/v]
Silica gel plate (Merck F 254)
Development with U.V. + Draggendorf reagent shows that the nitrile has disappeared.

The methanol is evaporated. The residue is taken up in 200 ml of distilled water and the insoluble matter is filtered off. This insoluble matter is taken up in anhydrous ethanol. The solution is dried over MgSO₄ and the MgSO₄ is filtered off. CRL 40236 is precipitated by means of a solution of hydrogen chloride in ether.

This hydrochloride is recrystallised from a mixture of ethyl acetate and methanol.

Weight = 12 g.
Yield = 52.8%.
Measured % Cl⁻ = 11.43%.
Theoretical % Cl⁻ = 11.88%.
Instantaneous melting point = 220° C.

EXAMPLE 6

2-(2,6-Dichlorobenzylamino)-pyrimidine hydrochloride

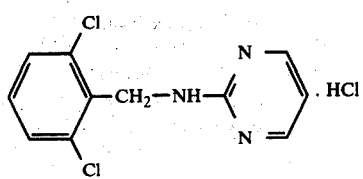

Code No: CRL 40243

10.5 g (0.125 mol) of sodium bicarbonate in 100 ml of distilled water are introduced into a solution of 38 g (0.4 mol) of 2-amino-pyrimidine at 90°-95° C., after which 19.55 g (0.1 mol) of 2,6-dichlorobenzyl chloride are introduced in 1 hour, and the mixture is then left at 90°-95° C. for 4 hours. It is cooled and the insoluble matter is filtered off and washed copiously with distilled water. This insoluble matter is recrystallised from ethyl acetate. Thereafter it is dissolved in hot ethyl acetate and the hydrochloride is precipitated by means of a solution of hydrogen chloride in ether.

Weight = 14 g.
Yield = 48%.
Measured % N = 4.70%.
Theoretical % N = 4.81%.
Instantaneous melting point = 188° C.

EXAMPLE 7

2-(2,6-Dichlorobenzyl-mercapto)-Δ²-imidazoline hydrochloride

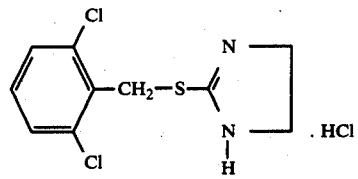

Code No: CRL 40255

A mixture consisting of 25 g (0.127 mol) of 2,6-dichlorobenzyl chloride, 12.9 g (0.127 mol) of 2-mercaptoimidazoline and a mixture of 62 ml of 95% strength ethanol and 30 ml of ethanol is heated under reflux for 3 hours. The mixture is filtered hot and the insoluble matter is washed with hot ethanol, dried and subjected to a nitrogen determination by means of perchloric acid.

Measured N%: 4.73%
Theoretical N% = 4.70%.

The product is dissolved in methanol at 40° C. and the hydrochloride is precipitated by means of 40 ml of a 3.5 N solution of hydrogen chloride in ether. The product is filtered off and dried. 21 g of CRL 40255 are obtained.

Yield = 55%.
Melting point = 260° C. (decomposition).
Measured % Cl⁻ = 11.79%.
Theoretical % Cl⁻ = 11.93%.

EXAMPLE 8

N-(2,6-Dimethylphenyl)-N'-hydroxy-guanidine hydrochloride

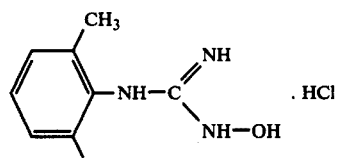

Code No.: CRL 40256

(a) N-(2,6-dimethylphenyl)-thiourea

A suspension of 0.6 mol (72.60 g) of 2,6-dimethylaniline in 600 ml of H₂O is brought into solution, whilst hot, by adding 0.66 ml (55 mol) of 12 N concentrated hydrochloric acid. 0.33 mol (25.08 g) of ammonium thiocyanate are added and the mixture is heated for 1 hour at 100° C. by means of an oil bath. It is cooled and stirred overnight. A precipitate appears. The mixture is cooled overnight in a refrigerator. The product is filtered off and washed with iced water. The expected thiourea is obtained.

Weight = 41.2 g.
Yield = 38%.

(b) 2,6-Dimethylphenyl-cyanamide

A suspension of 0.228 mol (41.2 g) of thiourea and 340 ml of water is heated to 100° C. A boiling solution of 2.28 mols of KOH (127.68 g) in 340 ml of H₂O is added. A hot saturated solution of 0.251 mol (95.18 g) of Pb(CH₃COO)₂. 3H₂O in water is added immediately and as rapidly as possible. The mixture is allowed to boil under reflux for 6 minutes and is cooled to 0° C. The PbS is filtered off. The filtrate is acidified with 150 ml of CH₃COOH. The cyanamide precipitates and is filtered off and washed with iced water.

Weight = 6.6 g.
Yield = 20%.

(c) CRL 40256

A solution of 0.108 mol of NH₂OH base in methanol is prepared by mixing, whilst cooling in an iced bath, solutions of 7.5 g (0.108 mol) of NH₂OH.HCl dissolved in methanol and of 5.83 g (0.108 mol) of NaOCH₃ dissolved in methanol. The NaCl is filtered off and the filtrate is introduced into an Erlenmeyer flask with magnetic stirring and cooling by means of an ice bath. 8 g (0.054 mol) of the preceding cyanamide are introduced and the mixture is stirred for 8 hours at 5° C. and overnight at ambient temperature. A thin layer chromatogram [eluant: CH₃OH:acetone (50:50); silica gel plate (Merck F 254); development: U.V. + Draggendorf reagent] shows that the cyanamide has disappeared. The methanol is evaporated and the residue is taken up in distilled water.

The mixture is extracted first with ether and then with ethyl acetate. The pH is adjusted to 11 with NaOH; the mixture is extracted with ether and then with ethyl acetate. An equal volume of sodium hydroxide solution is added to the aqueous phase and the mixture is extracted with ether and then with ethyl acetate. A thin layer chromatogram shows that these six fractions, thus obtained, are of identical composition; they are combined and dried over MgSO₄ in the presence of carbon black over the weekend.

They are filtered and the filtrate is poured into 11 ml of a 5 N solution of hydrogen chloride in ether. The hydrochloride precipitates in the form of an oil. The oil is decanted into a round-bottom flask and is dried in a desiccator for 24 hours in the presence of P₂O₅ and KOH. Finally, this oil crystallises. The chlorine content is determined:

Measured % Cl⁻ = 14.96%
Theoretical % Cl⁻ = 16.47%
Theoretical % Cl⁻ for the monohydrate product = 15.20%

The solid (4.30 g) is dissolved in 43 ml of water. The solution is filtered and the insoluble matter (0.270 g) is discarded. The aqueous phase has a volume of 45 ml.

One milliequivalent, namely 215.5 mg, representing 2.403 ml of solution, is removed by means of a pipette and the chlorine is determined as a check.

Measured % Cl⁻ = 15,81%.
Theoretical % Cl⁻ = 16.47%.
Theoretical % Cl⁻ (monohydrate) = 15.20%. 4.03 g of CRL 40256 are thus obtained.
Yield = 34.7%.

The purity of the product is about 95%.

EXAMPLE 9

2-(3,5-Dimethoxyphenoxy-methyl)-Δ²-imidazoline hydrochloride

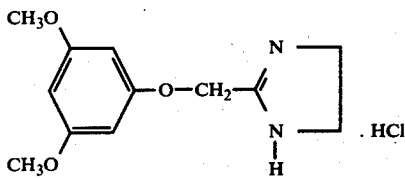

Code No: 40264

(a) 87.15 g (0.451 mol) of 3,5-dimethoxyphenoxy-acetonitrile are dissolved in 200 ml of anhydrous chloroform dried over CaCl₂. The mixture is cooled in an ice bath and 23 g (0.50 mol) of anhydrous ethanol are introduced. HCl gas is bubbled in until the mixture is saturated. The precipitate is filtered off, washed with anhydrous benzene and dried in a desiccator in the presence of KOH and P₂O₅. The corresponding imino-ethyl-ether is obtained.

Weight = 50 g.
Yield = 40.3%.

(b) CRL 40264

27.55 g (0.1 mol) of the hydrochloride of the iminoether obtained above are dissolved in 100 ml of anhydrous ethanol. A solution of 6.6 g (0.11 mol) of ethylenediamine in anhydrous ethanol is added dropwise and the mixture is heated under reflux for 2 hours and cooled. The solvent is evaporated. The residue is taken up in distilled water. The solution is extracted with ethyl acetate and the latter is dried over MgSO₄ and filtered. The hydrochloride is precipitated by means of a solution of hydrogen chloride in ether, and is filtered off and recrystallised from a mixture of acetone and ethanol (50:50 v/v).

Weight = 14 g.
Yield = 51%.
Measured % Cl⁻ = 13.20%
Theoretical % Cl⁻ = 13.02%.

EXAMPLE 10

N-(2,6-Dichlorophenyl)-N'-hydroxy-guanidine hydrochloride

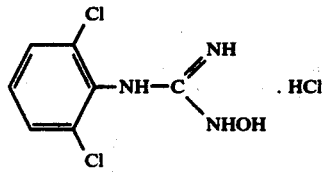

Code No: CRL 40306

A solution of 34.7 g (0.5 mol) of hydroxylamine hydrochloride in methanol and a solution of 27 g (0.5 mol) of sodium methylate in methanol is mixed whilst cooling by means of an ice bath. The NaCl is filtered off and the filtered solution is introduced into a 2,000 ml Erlenmeyer flask with magnetic stirring and cooling by means of an ice bath. A solution of 39.6 g (0.21 mol) of 2,6-dichlorophenyl-cyanamide in CH₃OH is run into the preceding solution and the mixture is stirred at ambient temperature (15°-25° C.) overnight. A small amount of insoluble matter is filtered off. To the methanol solution is added twice its volume of distilled water. An insoluble material is filtered off and discarded. The filtrate is placed in a freezer for 3 hours and an insoluble material is filtered off and discarded. The filtrate is evaporated to dryness. The residue is taken up in 1,000 ml of water and the medium is rendered acid with concentrated HCl. An insoluble material is filtered off and discarded. The liquid phase is washed with ether and the pH is brought to 8 with NaOH, taking care not to exceed this value. The mixture is extracted with ether. The ether is dried over MgSO₄ and the hydrochloride of the product is precipitated from the ether by bubbling-in HCl gas.

27.6 g of CRL 40306 are obtained.

Yield = 51%.
Melting point = 200° C.
Measured % Cl⁻ = 13.34%.
Theoretical % Cl⁻ = 13.84%.

EXAMPLE 11

(2,6-Dichlorobenzylamino)-acetamidoxime dihydrochloride

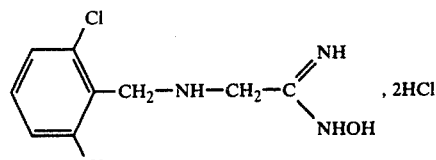

Code No: CRL 40344

(a) n-(2,6-Dichlorobenzyl)phthalimide

A mixture of 100 g. (0.15 mole) of 2,6-dichlorobenzylchloride and 103.6 g (0.56 mole) of potassium phthalimide in 400 ml of dimethylformamide is stirred under reflux and then cooled. The insoluble material is filtered off and washed with distilled water.

(b) 2,6-Dichlorobenzylamine

The insoluble product of the preceding stage is dissolved in 500 ml of 95% ethanol. 29.4 g (0.56 mole) of 98% hydrazine hydrate is added and the mixture is refluxed for 2 hours. It is then acidified with concentrated hydrochloric acid. The insoluble material is filtered off and discarded. The filtrate is diluted with water, neutralised with sodium hydroxide solution, and extracted with ethyl acetate. The aqueous phase is discarded and the ethyl acetate extract is washed with distilled water and then dried over anhydrous magnesium sulphate. After removal of the latter, the ethyl acetate is evaporated to give the desired product.

(c) 2,6-Dichlorobenzylamino acetonitrile

The product of the preceding state is dissolved in 200 ml of anhydrous ethanol 34 g (0.45 mole) of chloroacetonitrile and 50 ml of pyridine are added and the mixture is then heated under reflux for 6 hours. After cooling and evaporation of the ethanol, the residue is taken up in distilled water and the aqueous solution is extracted with ethyl acetate. The extract is washed with distilled water, dried over anhydrous magnesium sulphate and evaporated. The residue is taken up in methanol.

(d) CRL 40344

The methanolic solution obtained as just described is added to a solution of 1 mole of hydroxylamine in methanol. The mixture is stirred at ambient temperature overnight and the methanol is then evaporated. The residue is taken up in distilled water and extracted with ethyl acetate. The extract is dried over magnesium sulphate and the hydrochloride of the desired product is precipitated by passing in hydrogen chloride gas. The solid product is recrystallised from a mixture of acetone:anhydrous ethanol (50:50 v/v). The product weighs 3.4 g, an overall yield of 2.1%, and melts at 174° C.

EXAMPLE 12

(3,5-Diethoxyphenoxy)-acetamidoxime hydrochloride

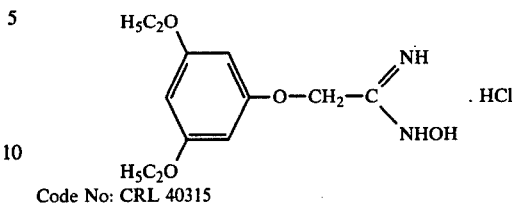

Code No: CRL 40315

(a) (3,5-Diethoxyphenoxy)-acetonitrile 18.2 g (0.1 mol) of 3,5-diethoxyphenol, 14 g (about 0.1 mol) of K₂CO₃, a few crystals of KI, 60 ml of anhydrous acetone and 10 ml (about 0.16 mol) of chloroacetonitrile are mixed in the cold in a 250 ml singleneck flask surmounted by a condenser.

The reaction mixture thus obtained is heated to the reflux temperature and the progress of the reaction is then followed by chromatography; a further 10 ml of chloroacetonitrile are added 2 hours after the start of refluxing. The mixture is kept under reflux for a further 2 hours and is then cooled, the acetone is evaporated in vacuo, the residue is taken up with water and extracted with ether, and the extract is washed with 1 N sodium hydroxide solution and then with water until the wash waters have a neutral pH. The ether phase is dried over MgSO₄ and the ether is evaporated. 19.9 g (90% yield) of a chromatographically pure oil are thus obtained.

(b) CRL 40315

0.09 mol of (3,5-diethoxyphenoxy)-acetonitrile is dissolved in 100 ml of 1-butanol and this solution is added, all at once, to a solution of 0.2 mol of hydroxylamine base in 20 ml of water (the hydroxylamine base being prepared by neutralising 14 g of hydroxylamine hydrochloride, in water, with 20 g of potassium bicarbonate). The reaction mixture is heated to the reflux temperature and the progress of the reaction is followed by chromatography.

After refluxing for 2 hours 30 minutes, the mixture is cooled, the 1-butanol is evaporated and the residue is taken up with water; the free base of CRL 40315 crystallises. It is filtered off and dried, and 21.4 g (yield: 94%) (instantaneous melting point = 138° C.) are obtained. CRL 40315 is obtained from a solution of the base in ethyl acetate by adding a solution of hydrogen chloride in ethanol and then recrystallising the product from ispropanol.

Weight: 20.8 g
Overall yield: 72%
Instantaneous melting point: 174°–176° C. (decomposition).

EXAMPLE 13

(3,4-Dichloroanilino)-acetamidoxime hydrochloride

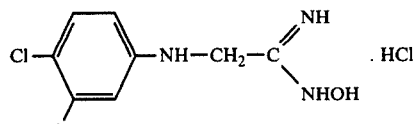

Code No: CRL 40375

(a) (3,4-Dichlorophenylamino)-acetonitrile 300 g of a 30% strength solution of formaldehyde are run into a solution of 1.5 mol (285 g) of sodium metabisulphite in 600 ml of water. The mixture is heated under reflux for 10 minutes. The solution is cooled, an insoluble material is filtered off and the volume is made up to 1,000 ml. a 3 M solution of the bisulphite compound of formaldehyde is obtained.

A suspension of 0.2 mol of 3,4-dichloroaniline in 100 ml of the preceding 3 M solution is heated under reflux until a homogeneous solution is obtained. Refluxing is then continued for 10 minutes and the mixture is cooled. A precipitate appears, which is filtered off, washed with iced water and with ethanol and then dried; 40 g (yield: 84%) of sodium 3,4-dichloroanilinomethyl-sulphate are obtained.

40 g of the preceding product are dissolved in 100 ml of hot water and a solution of 0.16 mol (10.4 g) of KCN in 20 ml of $H_2O$ is added. The mixture is heated under reflux for 1 hour. An oil appears, which crystallises on cooling. It is extracted with chloroform. The chloroform is dried over $MgSO_4$ and evaporated to dryness. The residue is taken up in methanol. A solution of (3,4-dichloroanilino)acetonitrile in methanol is thus obtained.

(b) CRL 40375

A solution of 0.3 mol of hydroxylamine base in methanol is prepared (from $NH_2OH.HCl$ + $NaOCH_3$). To this solution is added the solution of the nitrile in methanol, obtained above, and the mixture is stirred overnight at ambient temperature (15°–25° C.). The solution is evaporated to dryness. The residue is taken up in distilled water and extracted with ethyl acetate. The solvent is dried over $MgSO_4$ in the presence of carbon black. The hydrochloride is precipitated by means of a solution of hydrogen chloride in ethanol and is recrystallised from ethanol.

Weight: 18 g
Yield: 44%
Melting point: 160°–162° C.
Measured % $Cl^-$ = 13.40%
Theoretical % $Cl^-$: 13.12%.

The purity can, where necessary, be checked by thin layer chromatography (solvent: methanol:acetone (50:50 v/v); plate: silica gel (Merck F 254); development: U.V. + Draggendorf reagent).

EXAMPLE 14

(4-Chloroanilino)-acetamidoxime dihydrochloride

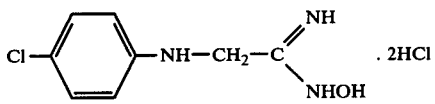

Code No: CRL 40424.

(a) (4-Chloroanilino)-acetonitrile

A mixture of 51 g (0.4 mol) of para-chloroaniline and 200 ml of 3 M solution of the bisulphite compound of formaldehyde is heated under reflux for 10 minutes and then cooled. The insoluble matter which has appeared is filtered off and washed with iced water and with ethanol.

The preceding salt, in a mixture of 200 ml of $H_2O$ and 28.60 g (0.44 mol) of KCN is heated under reflux for 40 minutes and then cooled. It is extracted with chloroform and the chloroform is dried over $MgSO_4$, filtered and evaporated. The residue is taken up in methanol. A solution of (4-chloroanilino)-acetonitrile in methanol is thus obtained.

(b) CRL 40424

The preceding solution is treated with a solution of 0.88 mol of hydroxylamine base in methanol, prepared by the action of 55.60 g of hydroxylamine hydrochloride on 43.20 g of sodium methylate. The mixture is stirred overnight at ambient temperature. 200 ml of $H_2O$ are added to the solution and the methanol is evaporated. The residue is extracted with ethyl acetate and the hydrochloride of the product is precipitated from the ethyl acetate solution, after the latter has been dried, by means of a solution of hydrogen chloride in ethanol. The hydrochloride is recrystallised from a mixture of ethanol and ethyl acetate (50:50 v/v).

Weight: 24.5 g
Overall yield: 24%
Melting point: 150° C.
Measured % $Cl^-$: 26.02%
Theoretical % $Cl^{31}$: 26.05%

EXAMPLE 15

(3-Fluoroanilino)-acetamidoxime dihydrochloride

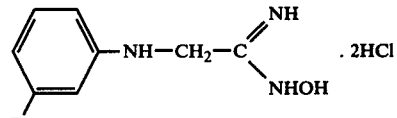

Code No: CRL 40469

This compound is obtained in an overall yield of 10% by employing the following reaction mechanism:

$$HCHO + KCN \longrightarrow HO-CH_2-CN$$

$$C_6H_5SO_2Cl + HO-CH_2-CN \longrightarrow C_6H_5SO_3CH_2CN$$

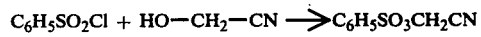

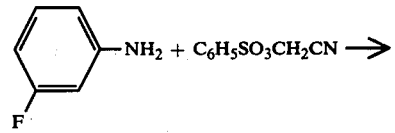

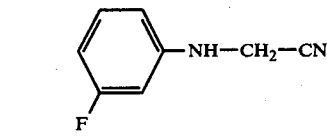

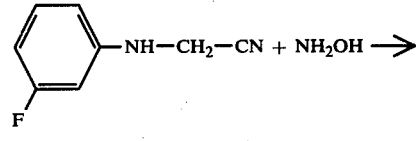

Melting point: 126°–128° C.
Measured % $Cl^-$: 27.86%
Theoretical % $Cl^-$: 27.73%.

The purity is controlled by thin layer chromatography (eluant: toluene:acetone:ammonia (30:70:2 v/v); plate: silica gel (Merck F 254); development: U.V. + Draggendorf reagent).

The results of the pharmacological tests which were carried out with the products of the formula I have been summarised below.

CRL 1752 (Example 1)

For intravenous administration to mice, this product has an LD-50 of 90 ± 3 mg/kg, the LD-0 being of the order of 75 mg/kg.

The hypotensive properties were studied on rats (four animals with normal blood pressure and two hypertensive animals), each animal receiving 100 mg/kg of CRL 1752 orally. On average, the arterial pressure is reduced by 20%, return to the normal pressure is observed in 3 hours 30 minutes and the pulse rate is not significantly altered.

CRL 40089 (Example 3)

This product is active on the central nervous system.

Interaction with apomorphine

Batches of 6 rats are given a subcutaneous injection of apomorphine (0.5 mg/kg) 30 minutes after the administration of CRL 40089.

CRL 40089 does not alter the intensity and duration of the stereotypies induced by apomorphine.

Interaction with amphetamine 30 minutes after the administration of CRL 40089, rats (6 per dose) are given an intraperitoneal injection of 2 mg/kg of amphetamine.

From a dose of 0.25 mg/kg upwards, CRL 40089 causes an increase in the duration of the amphetamine-induced stereotypies. This effect appears clearly from a dose of 1 mg/kg upwards.

In order to verify whether this boosting of the effects of amphetamine was a true effect or due to a blockage of the degradation of the amphetamine, the action of CRL 40089 in the presence of SKF 525 A (12 animals per dose) was investigated.

CRL 40089 boosts the duration of the stereotypies produced by the combination of amphetamine and SKF 525 A.

Interaction with reserpine 4 hours after the intraperitoneal administration of 2.5 mg/kg of reserpine, the mice are given CRL 40089 (6 animals per dose).

1. Action on the temperature

At doses of 0.5 and 2 mg/kg, CRL 40089 exerts a very partial antagonism against hypothermia induced by reserpine.

2. Action on ptosis

From a dose of 0.5 mg/kg upwards, CRL 40089 causes an increase in the palpebral ptosis induced by reserpine. This effect has a quasi-maximum at 2 mg/kg.

Interaction with oxotremorine 30 minutes after the administration of CRL 40089, the mice (6 per dose) are given an injection of oxotremorine (0.5 mg/kg administered intraperitoneally).

1. Action on the temperature

From a dose of 0.5 mg/kg upwards, CRL 40089 counteracts the hypothermia-inducing effect of oxotremorine.

Oxotremorine produces extensive mortality in mice which have CRL 40089 at a dose of 32 mg/kg.

2. Action on trembling movements

CRL 40089 does not modify the intensity of the trembling movements produced by oxotremorine.

3. Action on the peripheral cholinergic symptoms

CRL 40089 virtually does not modify the exaggeration of the lachrymal and salivary secretions and of the defaecation which appears in mice which have received an injection of oxotremorine.

Action on the four plate test, the traction and the electric shock

The test is carried out on batches of 10 sensitive mice (IVIC CEBA) 30 minutes after the administration of CRL 40089.

CRL 40089 does not alter the number of incorrect moves which are punished (by electric shock), does not cause a major motor incapacity and does not counteract the convulsive effects of the electric shock, but aggravates its lethal effects (8 to 32 mg/kg).

Action on the motility

1. Spontaneous motility

The motility of the mice is recorded 30 minutes after the administration of CRL 40089 (6 animals per dose, 12 control animals).

From a dose of 0.5 mg/kg upwards, CRL 40089 causes a decrease in the locomotion. This effect increases with the dose of CRL 40089.

2. Residual motility

After remaining for 18 hours in the actimeters, the mice (6 per dose, 12 control animals) receive CRL 40089 and the recording of the motility starts 30 minutes after the administration of the product.

CRL 40089 does not cause a marked modification of the motility of mice accustomed to their cage.

3. Motor recovery after hypoxia

The mice (10 per dose, 20 control animals) are subjected to anoxia, by pressure reduction, 30 minutes after the administration of CRL 40089 and their motility is then recorded for 10 minutes.

CRL 40089 does not produce an improvement in the motor recovery of mice suffering from anoxia.

Action on the inter-group aggressiveness

Batches of 3 mice which have remained separate for 3 weeks in each of the halves of a single cage, are brought together 30 minutes after having received CRL 40089 and the number of fights which take place in the course of the next 15 minutes is recorded.

At all the doses tested, CRL 40089 inhibits the aggressive behaviour of the mice.

In conclusion, CRL 40089 is an anti-depressant of moderate intensity, having sedative effects and effects on the peripheral sympathetic excitation.

CRL 40306 (Example 10)

This product, which has hypotensive properties, was studied in rats with normal blood pressure, using a first batch of five animals each of which receive (a) a first dose (100 mg/kg) of CRL 40306 administered orally.

The arterial pressure of the animals on average changes from 114 to 84 mm Hg, that is to say a change of −24%, in 1 hour (significant to 5% at this moment, though one of the rats does not exhibit hypotension. If the percentage variation is calculated for the four rats which react, a hypotension of 31% is found). The arterial pressure thereafter rises again progressively and is 94 mm Hg 2 hours after administration of the product; it remains at this level for 4 hours (−18%, not significant).

Their pulse rate changes from 480 to 330 beats/minute over the course of 30 minutes, remains at this level for 2 hours (−28%, significant to 5%) and then rises again progressively, reaching 460 beats/minute after 4 hours. All the rats exhibited bradycardia.

(b) A second dose (100 mg/kg), 4 hours later, administered orally.

The arterial pressure changes to 80 mm Hg (−29% relative to the start of the experiment) in the course of 30 minutes and remains thereat for longer than the 2 hours for which the observation lasts (significant to 1%). All the rats exhibit hypotension. The pulse rate does not decrease, as after the first administration, and changes merely to 420 beats/minutes (−13%, not significant).

A second batch of rats received CRL 40306 orally at doses of 10 mg/kg administered six times, at intervals of 30 minutes.

The arterial pressure progressively decreases after each administration; this hypotension is significant to 5% for the overall dose of 30 mg/kg (the arterial pressure changes on average from 108 to 84 mm Hg, representing −20%) to 1% for 40 mg/kg (−26%, minimum arterial pressure reached: 78 mm Hg), and to $1°/_{oo}$ for 50 mg/kg (same hypotension, but more regular effect).

The heart beat decreases as from the first administration but this bradycardia is not significant except at a dose of 40 mg/kg upwards (−20%, equivalent to the change from 455 to 360 beats/minute); the supplementary dose of 10 mg/kg no longer has a bradycardia-inducing effect.

A supplementary dose of 50 mg/kg produces a somewhat lesser hypotension (−29%, minimum level reached: 75 mm Hg, significant to $1°/_{oo}$, for more than 2 hours).

The heart beat decreases after 30 minutes by 24% over the course of less than 1 hour (significant to 5%).

The hypotensive action of the single dose of 100 mg/kg administered orally was confirmed on 8 rats with normal blood pressure. The arterial pressure decreases by an average of 22% — it changes from 113 to 86 mm Hg over the course of 30 minutes; this effect is significant to 1% and lasts for 5 hours, at which time the arterial pressure has returned to 102 mm Hg.

The heart beat of all the animals decreases; it changes on average from 420 to 350 beats/minute, amounting to −17%, significant to 1%, over the course of 2 hours. The heart beat has returned to its starting level after 3 hours.

The experiments carried out on conscious dogs and on dogs anaesthesised with Nembutal show that CRL 40306 is a hypotensive substance which acts at the ganglion lvel (decreased D.M.P.P), on the one hand, and at the level of the sympathic nerve ends (α-blocking effect) on the other.

CRL 40344 (Example 11)

At a dose of 100 mg/kg administered orally, this product lowers the arterial pressure of conscious rats, with normal blood pressure, by about 20%.

CRL 40315 (Example 12)

This product has been studied in suspension in a gummy solution (gum arabic) which is administered intraperitoneally in a volume of 20 ml/kg, to mice.

Pre-toxicity

At high doses, namely 256 mg/kg, 512 mg/kg and 1,024 mg/kg, sedation with trembling movements is observed. The LD-O is greater than 256 mg/kg in mice.

Action on the motility (1) Spontaneous motility

Thirty minutes after administration of CRL 40315, a decrease, by half, of the spontaneous motility is observed.

(2) Residual motility

After 18 hours in the actimeters, the mice receive CRL 40315 (6 animals per dose, 12 control animals) and, following 30 minutes without recording, their motility is observed for 30 minutes. At a dose of 32 mg/kg, CRL 40315 results in a resumption of the activity in mice accustomed to their cage.

(3) Motor recovery after hypoxia aggression

Thirty minutes before being subjected to anoxia by pressure reduction, the mice (10 per dose, 20 control animals) recive CRL 40315, and their motility is then noted for 10 minutes. Using this technique, it is found that there is no motor improvement in mice which have been subjected to anoxia by pressure reduction.

CRL 40375 (Example 13)

This product was administered in aqueous solution in a volume of 5 ml/kg to rats and of 20 ml/kg to mice.

Toxicity

The LD-50 of CRL 40375 administered orally to male rats is 245 mg/kg. Administered orally to mice, CRL 40375, at doses of 512 mg/kg and 1,024 mg/kg, causes the appearance of pre-convulsive trembling movements and then clonic convulsions, followed by death, respectively 45 minutes (at 512 mg/kg) and 20 minutes (at 1,024 mg/kg) after administration. In mice, the LD-0 for oral administration is greater than 128 mg/kg.

Action on the central nervous system

At high doses, CRL 40375 causes a prolongation of amphetamine-induced stereotypies in rats. At doses of 32 and 128 mg/kg, CRL 40375 moderately opposes the hypothermia-inducing action of oxotremorine. Finally, in mice, it decreases the spontaneous motility.

Action on the arterial pressure

In conscious rats, with spontaneous hypertension, the measurements of the arterial pressure gave the following results:
(a) using a non-surgical method, at an orally administered dose of 10 mg/kg/day for 5 days, a maximum hypotension of 16% reached from the first 24 hours onwards is observed;
(b) using a surgical method, the orally administered dose of 5 mg/kg of CRL 40375 produces a significant hypotension of 12%; the maximum orally administered hypotensive dose is 5 mg/kg, but it is necessary to use a dose of 10 mg/kg in order still to observe a hypotensive effect after 24 hours.

In conscious rats with normal blood pressure (using a non-surgical method), CRL 40375, given intravenously at successive doses of 0.5, 1 and 2.5 mg/kg, possesses a hypotensive effect which lasts for more than 24 hours, and the symptom of relaxation of the nictitation membrane also lasts several days.

In conscious dogs or dogs anaesthesised with Nembutal, CRL 40375 administered orally acts as a hypotensive agent at a dose of 5 mg/kg.

In rabbits anaesthesised with Nembutal, CRL 40375 acts as a hypotensive agent at a dose of 10 mg/kg administered intravenously.

In man, CRL 40375a, given in the form of pills, tablets or injectable ampoules, gave good results in the treatment of hypertension, when used at the rate of 1 to 2 ampoules per day containing 5 mg of CRL 40375, and of 1 to 2 tablets or pills per day each containing 10 mg of CRL 40375.

CRL 40424 (Example 14)

CRL 40424 in solution in distilled water was administered intraperitoneally in a volume of 20 mg/kg to mice, and of 5 ml/kg to rats.

Toxicity

In mice, the LD-0 is greater than 256 mg/kg. In rats, for oral administration, the LD-50 is 450 mg/kg.

Action on the central nervous system

In rats, CRL 40424 has a sedative effect, with hypomotility and decrease in the aggressiveness; it boosts the amphetamine-induced stereotypies and exhibits moderate antagonism to hypothermia brought about by oxotremorine.

Action on the arterial pressure

In conscious rats with spontaneous hypertension CRL 40424 has a hypotensive action when administered orally at a dose of 10 mg/kg/day.

In man, in the form of pills containing 10 mg, taken 2 to 3 times per day, CRL 40424 gives excellent results as a hypotensive agent.

CRL 40469 (Example 15)

The hypotensive action of CRL 40469 has been demonstrated in conscious rats with spontaneous hypertension.

At a dose of 100 mg/kg administered orally, CRL 40469 causes a decrease in the arterial pressure in all the animals (test batches of 7 rats), which on average changes in the course of 30 minutes from 165 to 110 mm Hg, representing −31% (a significant decrease), remains at this level for 5 hours and then shows a slight further percentage decrease (−32%); the heart beat decreases (−5%) after 1 hour 30 minutes.

At a dose of 40 mg/kg administered orally, 2 hours after the first administration, the arterial pressure decreases in all the animals (6 rats) and changes on average from 165 to 120 mm Hg, representing −28% (a significant decrease) and remains at this level for 5 hours (duration of the observations); the heart beat does not change and remains at 370 beats/minute.

At a dose of 10 mg/kg administered orally, to a test batch of 6 rats, it is found that the arterial pressure of 5 rats shows no change, the 6th rat being the only one to show a decrease (−30%) of the arterial pressure, in 1 hour.

I claim:

1. A phenyl-amidoxime of the formula:

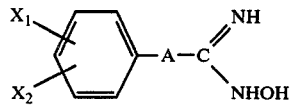

wherein A represents —CH$_2$—, —CHOH—, —CH$_2$O—, —CH$_2$S—, —OCH$_2$—, —SCH$_2$—, —NHCH$_2$—, —NHCOCH$_2$—, or —CH$_2$NHCH$_2$—, X$_1$ represents hydrogen, halogen, C$_1$-C$_4$-alkyl or C$_1$-C$_4$-alkoxy, X$_2$ represents halogen, C$_1$-C$_4$-alkyl or C$_1$-C$_4$-alkoxy.

2. A phenyl-amidine according to claim 1 in which X$_1$ is hydrogen, Cl, F, CH$_3$, OCH$_3$, or OC$_2$H$_5$ and X$_2$ is Cl, F, CH$_3$, OCH$_3$, or OC$_2$H$_5$.

3. A phenyl-amidine derivative according to claim 1, wherein A is —NHCH$_2$—.

4. (3,4-Dichlorophenyl)-acetamidoxime.
5. (2,6-Dichloroformanilido)-acetamidoxime.
6. (2,6-Dichlorobenzylamino)-acetamidoxime.
7. (3,5-Diethoxyphenoxy)-acetamidoxime.
8. (3,4-Dichloroanilino)-acetamidoxime.
9. (4-Chloroanilino)-acetamidoxime.
10. (3-Fluoroanilino)-acetamidoxime.
11. A therapeutic composition, comprising at least one compound according to claim 1 in association with a physiologically acceptable excipient.

* * * * *